(12) United States Patent
Zhang et al.

(10) Patent No.: US 11,892,432 B2
(45) Date of Patent: Feb. 6, 2024

(54) MULTIFUNCTIONAL ROCK MECHANICS TESTER

(71) Applicant: Chengdu University of Technology, Chengdu (CN)

(72) Inventors: Chen Zhang, Chengdu (CN); Huaguo Wen, Chengdu (CN); Chao Ma, Chengdu (CN); Jintong Liang, Chengdu (CN); Yiquan Ma, Chengdu (CN); Yixin Dong, Chengdu (CN); Xiangye Kong, Chengdu (CN); Xin Wang, Chengdu (CN); Shaohui Wang, Chengdu (CN); Gang Zhou, Chengdu (CN); Yuan Zhong, Chengdu (CN); Wenbin Tang, Chengdu (CN); Jing Nie, Chengdu (CN); Bolin Zhang, Chengdu (CN); Yunchuan Zeng, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 18/358,611

(22) Filed: Jul. 25, 2023

(65) Prior Publication Data
US 2023/0400396 A1      Dec. 14, 2023

(30) Foreign Application Priority Data

Jun. 13, 2022    (CN) .......................... 202210659278.4

(51) Int. Cl.
*G01N 3/12*     (2006.01)
*G01N 33/24*    (2006.01)

(52) U.S. Cl.
CPC ............... *G01N 3/12* (2013.01); *G01N 33/24* (2013.01)

(58) Field of Classification Search
CPC .................................. G01N 3/12; G01N 33/24
See application file for complete search history.

(56) References Cited

U.S. PATENT DOCUMENTS

| 9,488,560 B2 * | 11/2016 | Liu .......................... G01N 3/32 |
| 11,067,488 B1 * | 7/2021 | Zhao ......................... G01N 3/12 |
| 2020/0103322 A1 * | 4/2020 | Regimand ................ G01N 3/08 |

FOREIGN PATENT DOCUMENTS

| CN | 1991332 A * | 7/2007 |
| CN | 206378363 U | 8/2017 |

(Continued)

*Primary Examiner* — Natalie Huls
(74) *Attorney, Agent, or Firm* — Nitin Kaushik

(57) ABSTRACT

The present invention provides a multifunctional rock mechanics tester, pertaining to the technical field of mechanics tester, consisting of a base; wherein a power mechanism is mounted on the top of the base, two tension testing mechanisms are arranged on the power mechanism in an up-and-down symmetrical way, a clamping mechanism is mounted on each tension testing mechanism, a rock testing block is clamped between the two clamping mechanisms. The present invention realizes the tension and pressure testing of the rock test block through the arrangement of tension testing mechanism and pressure testing mechanism, thus improving the functionality of the present mechanics tester, which not only reduces the testing cost, but also effectively decreases the occupied space; the present invention solves the problem that the traditional mechanics tester can only complete one kind of test when it is used.

8 Claims, 10 Drawing Sheets

(56) References Cited

FOREIGN PATENT DOCUMENTS

| CN | 105910909 B | * | 12/2018 |
| CN | 109752234 A | * | 5/2019 |
| CN | 209707244 U | * | 11/2019 |
| CN | 210626174 U | | 5/2020 |
| CN | 215179363 U | | 12/2021 |

* cited by examiner

MULTIFUNCTIONAL ROCK MECHANICS TESTER

CROSS-REFERENCE TO RELATED APPLICATIONS

The application claims priority to Chinese patent application No. 2022106592784, filed on Jun. 13, 2022, the entire contents of which are incorporated herein by reference.

TECHNICAL FIELD

The present invention pertains to the technical field of mechanics tester, in particular to a multifunctional rock mechanics tester.

BACKGROUND

Rock mechanics is a subject that studies the stress, strain, failure, stability and reinforcement of rocks under the action of external factors. The rock mechanics characteristics are usually tested with uniaxial compression tester, biaxial compression tester, tensile tester, etc.

However, one traditional mechanics tester can only perform one test and another tester is required to contact another test, which not only increases the test cost, but also increases the space occupied by multiple testers. When the clamping mechanism of traditional mechanics tester clamps the rock sample in the tensile test, the threaded rod of the clamping mechanism may get loose easily, making the clamping block loosened and thus reducing the reliability of the tester.

SUMMARY

In view of the above, the present invention provides a multifunctional rock mechanics tester. The tension and pressure testing of the rock test block are achieved through the arrangement of tension testing mechanism and pressure testing mechanism, thus improving the functionality of the present mechanics tester, which not only reduces the testing cost, but also effectively decreases the occupied space; a locking component is provided to effectively prevent the L-shaped clamping block from falling off, thus improving the reliability of the mechanics tester in the tensile test.

The invention provides a multifunctional rock mechanics tester consisting of a base, wherein a power mechanism is mounted on the top of the base, two tension testing mechanisms are arranged on the power mechanism in an up-and-down symmetrical way, a clamping mechanism is mounted on each tension testing mechanism, a rock testing block is clamped between the two clamping mechanisms, a controller is mounted on the right side of the power mechanism, a rectangular cavity is set at the lower part of the front end of the base and internally connected with a storage box in a sliding way, two pressure testing mechanisms are placed on the bottom of the storage box, a clamping mechanism is set on each pressure testing mechanism, two limit components are mounted on the power mechanism in an up-and-down symmetrical way, and a locking component is set on each clamping mechanism.

The tension testing mechanism comprises a connecting seat A, four first sliding sleeves, four first sliding pillars, a pull plate, a tension sensor and a connector plate A, wherein the connecting seat A is connected between two adjacent connecting slides in a sliding way and fixedly connected with the four first sliding sleeves at the top, each first sliding sleeve is internally connected a corresponding first sliding pillar in a sliding way, the pull plate is fixedly connected with the top of the four first sliding sleeves and provided with two second T chutes, the tension sensor is connected between the connecting seat A and the pull plate, the connector plate A (306) is arranged in the middle of the rear of the connecting seat A, and a rectangular socket is set on the top of the connector plate A;

The pressure testing mechanism comprises a rectangular support plate, a second sliding pillar, a sliding sleeve, a connecting seat B, a connector plate B and a pressure sensor, wherein four second sliding pillars are fixedly connected with the bottom of the rectangular support plate, a sliding sleeve is internally connected with each second sliding pillar in a sliding way, the connecting seat B is fixedly connected with the bottom of the four sliding sleeves, strip sliders are set on both sides of the connecting seat B, the connector plate B is arranged in the front end of the connecting seat B, a rectangular socket is set on the top of the connector plate B, the pressure sensor is arranged between the rectangular support plate and the connecting seat B, and two third T chutes are arranged on the rectangular support plate.

Optionally, a strip opening is made on both sides of the base and connected to the rectangular cavity; a limit sliding pillar is set on both ends of the storage box, and the two sliding pillars are connected with the two strip openings in a sliding way.

Optionally, the power mechanism comprises a support frame, a first hydraulic cylinder, a second hydraulic cylinder, two driving plates, a connecting slide and a baffle, wherein the support frame is fixedly connected to the top of the base, the first hydraulic cylinder and the second hydraulic cylinder are respectively mounted on the upper and lower sides of the support frame, and the control valves on the first hydraulic cylinder and the second hydraulic cylinder are electrically connected with the controller; the opposite end of the telescopic rods on the first hydraulic cylinder and the second hydraulic cylinder are fixedly connected with a corresponding driving plate, two connecting slides are mounted on the opposite sides of the two driving plates, a baffle is fixedly connected with each rear ends of two adjacent connecting slides, and two T sliders are arranged on each sides of each driving plate.

Optionally, two first T chutes are arranged on both sides inside the support frame, four vertical guide rods are symmetrically arranged on both sides inside the support frame and connected with two driving plates in a sliding way, and four T sliders on each driving plate are connected with four first T chutes inside the support frame in a sliding way.

Optionally, the clamping mechanism comprises two vertical support plates A, a clamping screw, two L-shaped clamping blocks and a limit gear, wherein the two vertical support plates A are fixedly connected to the pull plate, the clamping screw is rotatably connected between the two vertical support plates A, externally provided with two reverse threads in a left-to-right symmetrical manner, and externally connected with two L-shaped clamping blocks through the two reverse threads, two T sliders are set at the bottom of each L-shaped clamping block and connected with two second T chutes on the top of the pull plate in a sliding way, and the limit gear is mounted on the external right of the clamping screw.

Optionally, the clamping mechanism comprises two vertical support plates, a clamping screw, two clamping blocks and a box-shaped pad, wherein the two vertical support plates are fixedly connected to the rectangular support plate, the clamping screw is rotatably connected between the two vertical support plates, externally provided with two reverse threads in a left-to-right symmetrical manner, and externally connected with two clamping blocks through the two reverse threads, two T sliders are set at the bottom of each clamping block and connected with two third T chutes on the rectangular support in a sliding way, and the box-shaped pad is fixedly connected at the middle of the top of the rectangular support plate.

Optionally, the limit component comprises a limit housing, a limit slider and an L-shaped pull bar, wherein the limit housing is fixedly connected in the middle of the rear end of the driving plate and internally connected with the limit slider in a sliding way, the front side angle at the top of the limit slider is rounded, and the bottom of the limit slider is fixedly connected to an L-shaped pull bar that runs through the bottom of the limit housing and sleeved with a spring inside the limit housing; when the tension testing mechanism is mounted on the driving plate, the rear end of the connector plate A runs through the baffle, and the head end of the limit slider is inserted into the rectangular socket on the connector plate A.

Optionally, the locking component comprises a locking housing, a locking slider, two locking strips, a sliding groove, and a sliding pillar, wherein the locking housing is fixedly connected to the pull plate, internally connected to a locking slider in a sliding way and provided an L-shaped opening at the top, two locking strips are set at the rear of the locking slider and closely contacted with the outer peripheral surface of the limit gear at the rear, the front end of the locking slider is equipped with a guide rod that runs through the front side wall of the locking housing and is sleeved with a spring inside the locking housing, the top of the locking slider is equipped with a sliding groove which is internally connected to a sliding pillar in a sliding way, and the sliding pillar runs through the L-shaped opening on the locking housing.

Beneficial Effects

1. Compared with the traditional mechanics tester, the mechanics tester of each embodiment of the invention can test the tension and pressure of the rock sample with its tension testing mechanism and pressure testing mechanism in the whole test process, thus improving the functionality of the mechanics tester. Moreover, the rock mechanics tester can directly conduct another test after completing one test, unnecessary to arrange another tester, which not only reduces the testing cost, but also effectively decreases the occupied space.

2. A locking component is provided, wherein when the rock sample is gripped by the clamping mechanism, the rear end of the two locking strips can be closely contacted with the outer peripheral surface of the limit gear by sliding the sliding pillar to the back end of the L-shaped opening on the locking housing, so that the limit gear can be effectively locked to effectively prevent the clamping screw from loosening and the L-shaped clamping block from falling off, thus improving the reliability of the mechanics tester in the tensile test.

3. A limit component is provided, wherein when replacing the tension testing mechanism with the pressure testing mechanism, it is only necessary to manually pull the L-shaped pull bar towards the end to pull the limit slider end out from the rectangular socket on the connector plate A and make the connecting seat A not fix the two connecting slides, then slide the connecting seat A forward and remove it, slide the connecting seat B between the two connecting slides, thread the connector board B through the baffle, insert the top of the limit slider into the rectangular socket on the connector plate B, thus completing the replacement between the tension testing mechanism and the pressure testing mechanism, without any tools, thereby improving the operational convenience of the mechanics tester.

BRIEF DESCRIPTION OF DRAWINGS

In order to explain the technical solutions in the embodiments of the present invention more clearly, the following will make a brief introduction to the drawings of the embodiments.

The drawings in the following description are merely some embodiments of the present invention, but are not intended to limit the present invention.

In the drawings:

FIG. 1 is a schematic diagram of the mechanics tester structure according to embodiments of the invention;

FIG. 2 is a schematic diagram of the disassembled mechanics tester according to embodiments of the invention;

FIG. 3 is a schematic diagram of local section view of the support frame according to embodiments of the invention;

FIG. 4 is a schematic diagram of the tensile testing mechanism and the limit component according to embodiments of the invention;

FIG. 5 is a schematic diagram of the limit component according to embodiments of the invention;

FIG. 6 is a schematic diagram of the clamping mechanism and the locking component according to embodiments of the invention;

FIG. 7 is a schematic diagram of the clamping mechanism according to embodiments of the invention;

FIG. 8 is a schematic diagram of local section view of limit gear according to embodiments of the invention;

FIG. 9 is a schematic diagram of the dissembled locking housing and locking slider according to embodiments of the invention;

FIG. 10 is a schematic diagram of the dissembled clamping screw and clamping block according to embodiments of the invention.

EXPLANATION OF NUMBERS MARKED IN THE FIGURE

Figure 1:
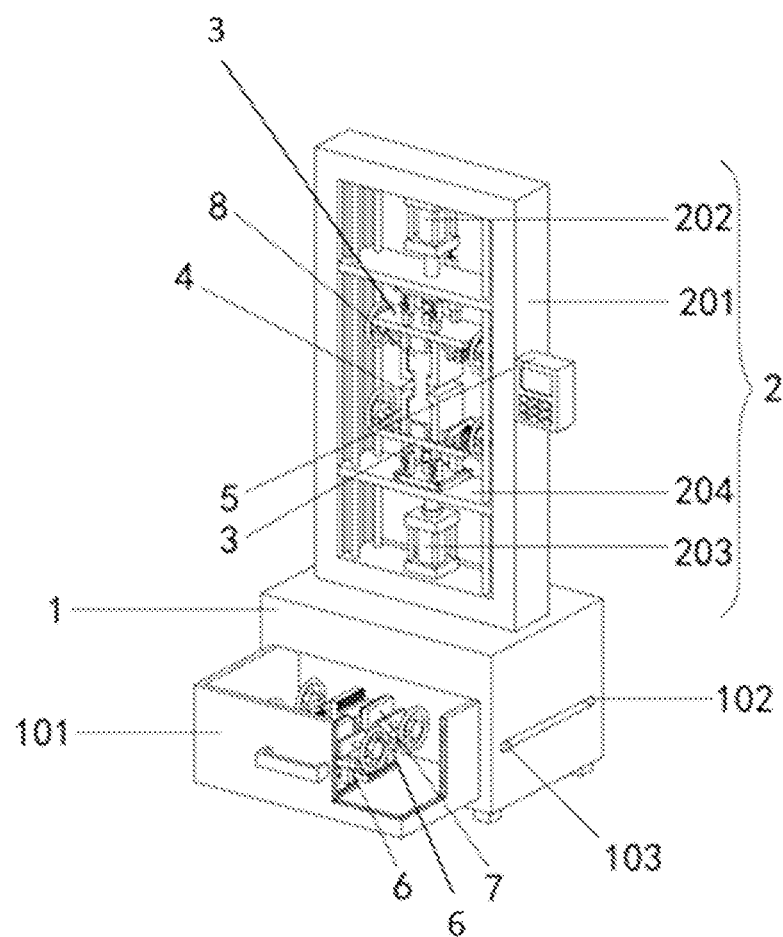
Figure 2:
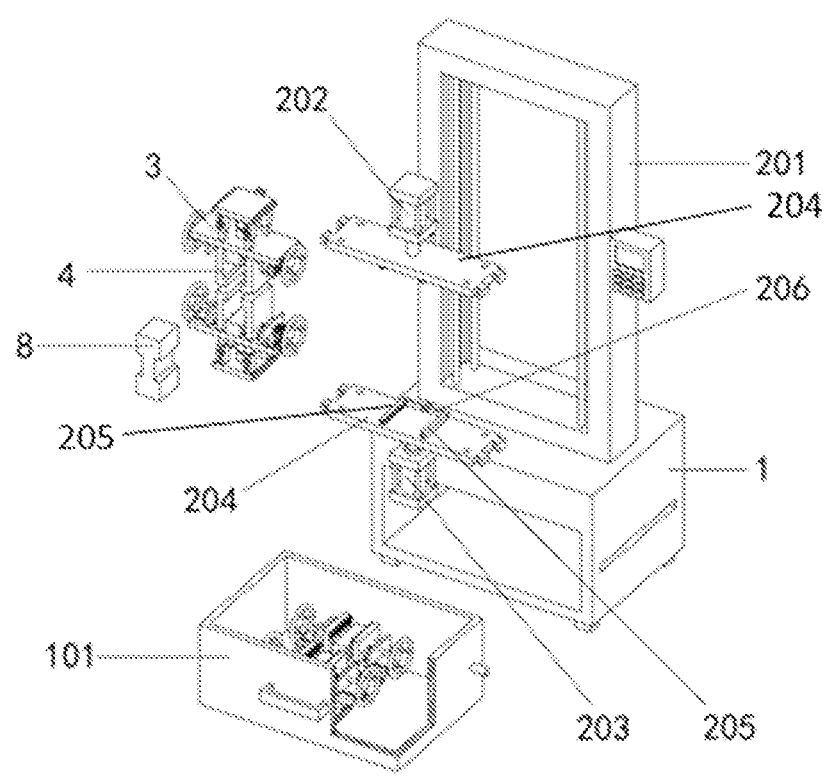

1. Base; 101. Storage box; 102. Strip opening; 103. Limit sliding pillar; 2. Power mechanism; 201. Support frame; 202. First hydraulic cylinder; 203. Second hydraulic cylinder; 204. Driving plate; 205. Connecting slide; 206. Baffle; 3. Tension testing mechanism; 301. Connecting seat A; 302. First sliding sleeve; 303. First sliding pillar; 304. Pull plate; 305. Tension sensor; 306. Connector plate A; 4. Clamping mechanism; 401. Vertical support plate A; 402. Clamping screw; 403. L-shaped clamping block; 404. Limit gear; 5. Controller; 6. Pressure testing mechanism; 601. Rectangular support plate; 602. Second sliding pillar; 603. Second sliding sleeve; 604. Connecting seat B; 605. Connector plate B; 606. Pressure sensor; 7. Clamping mechanism; 701. Vertical support plate B; 702. Clamping screw; 703. Clamping block; 704. Box-shaped pad; 8. Rock sample; 9. Limit component; 901. Limit housing; 902. Limit slider; 903. L-shaped pull bar; 10. Locking component; 1001. Locking housing; 1002. Locking slider; 1003. Locking strip; 1004. Sliding groove; 1005. Sliding pillar.

DETAILED DESCRIPTION OF THE EMBODIMENTS

In order to make the purpose, technical solutions and advantages of the present invention more clearly understood, the technical solutions of the embodiments of the present invention will be described expressly and integrally in conjunction with the appended figures of the embodiments of the present invention. Unless otherwise stated, the terms used herein have the meanings commonly associated with the art. Identical numbers in the drawings represent identical components.

Embodiments: Please Refer to FIGS. 1 to 10

Figure 3:
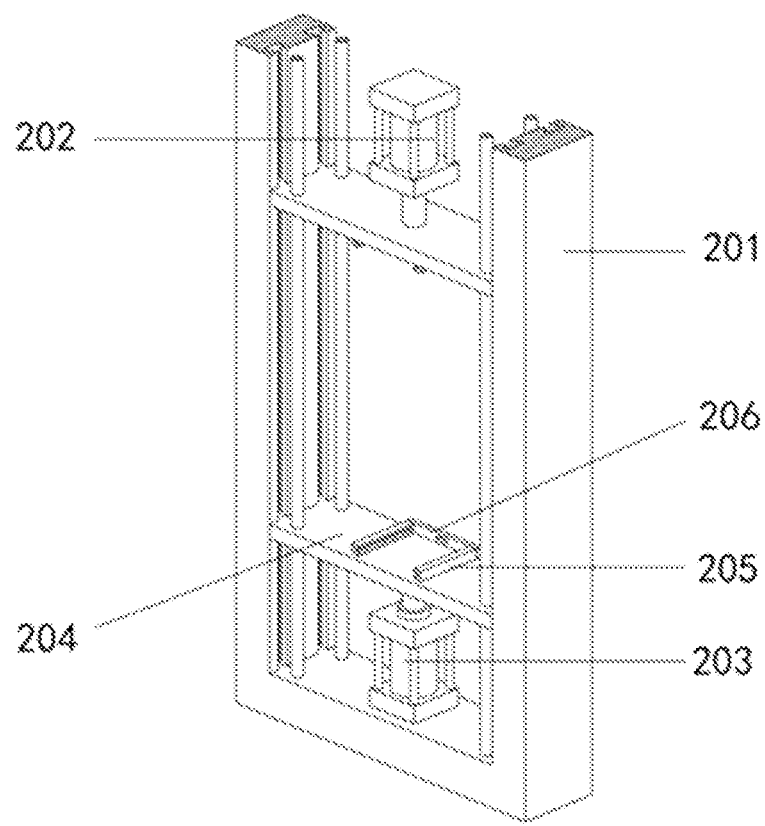
Figure 4:
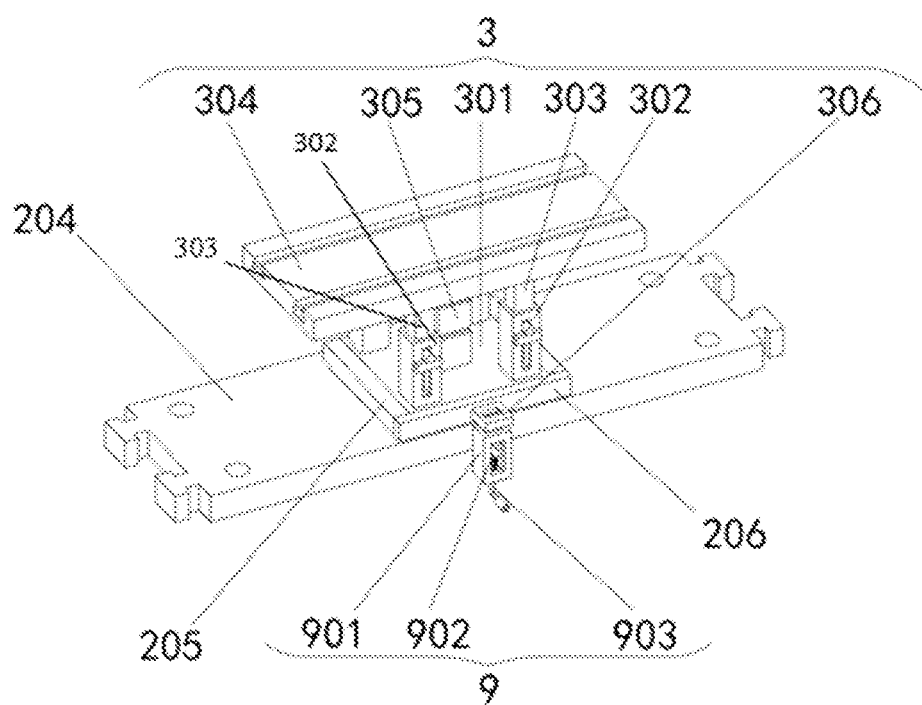
Figure 5:
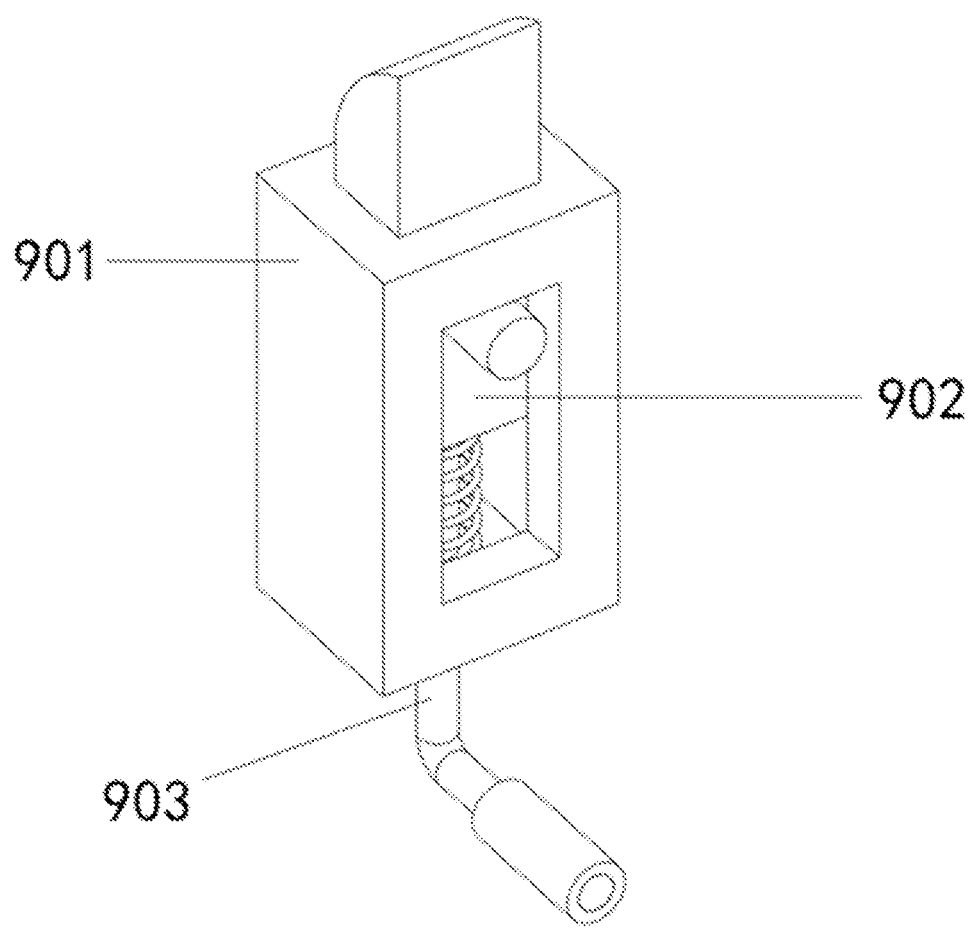
Figure 6:
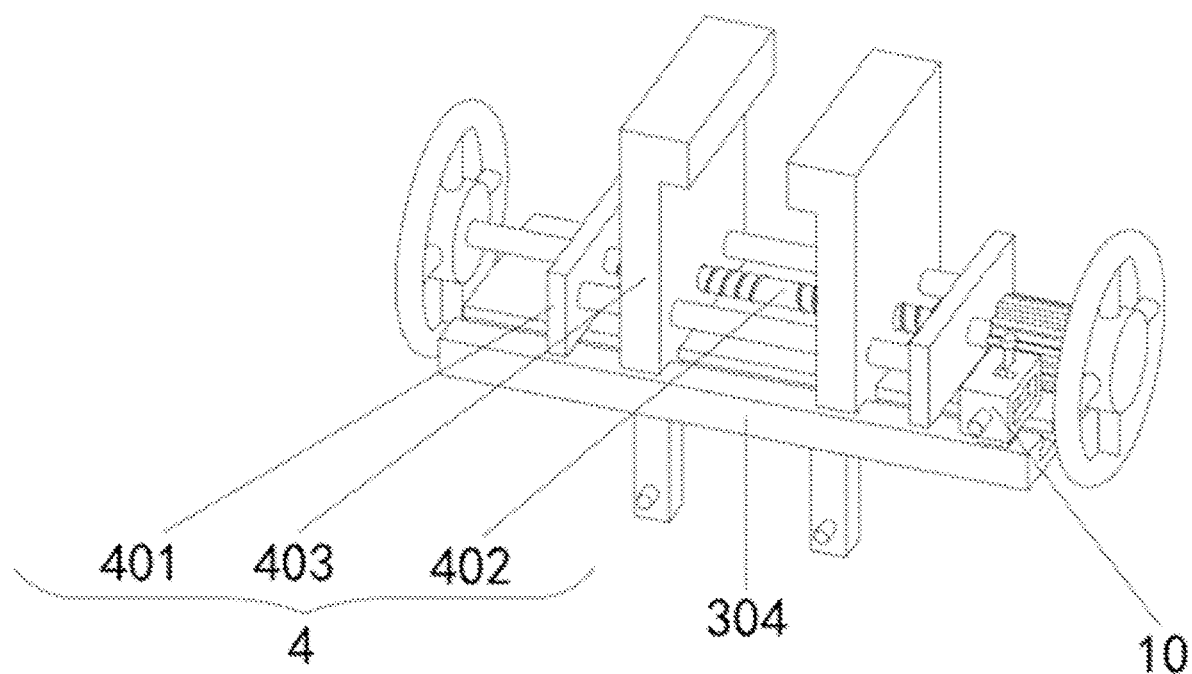
Figure 7:
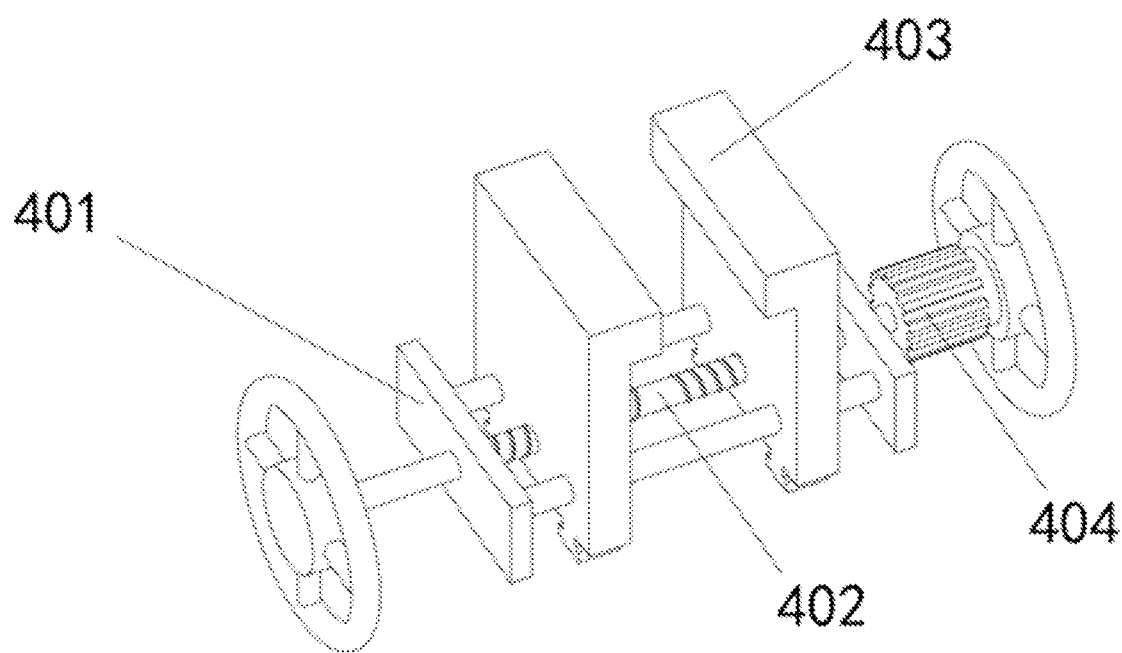
Figure 8:
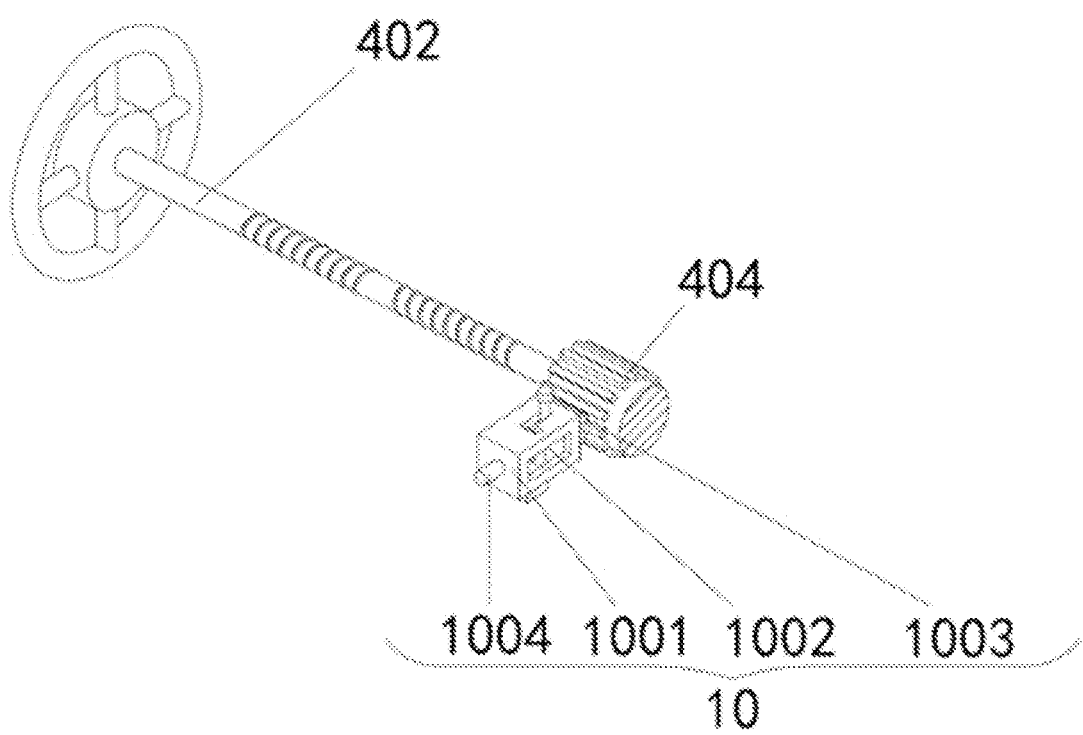
Figure 9:
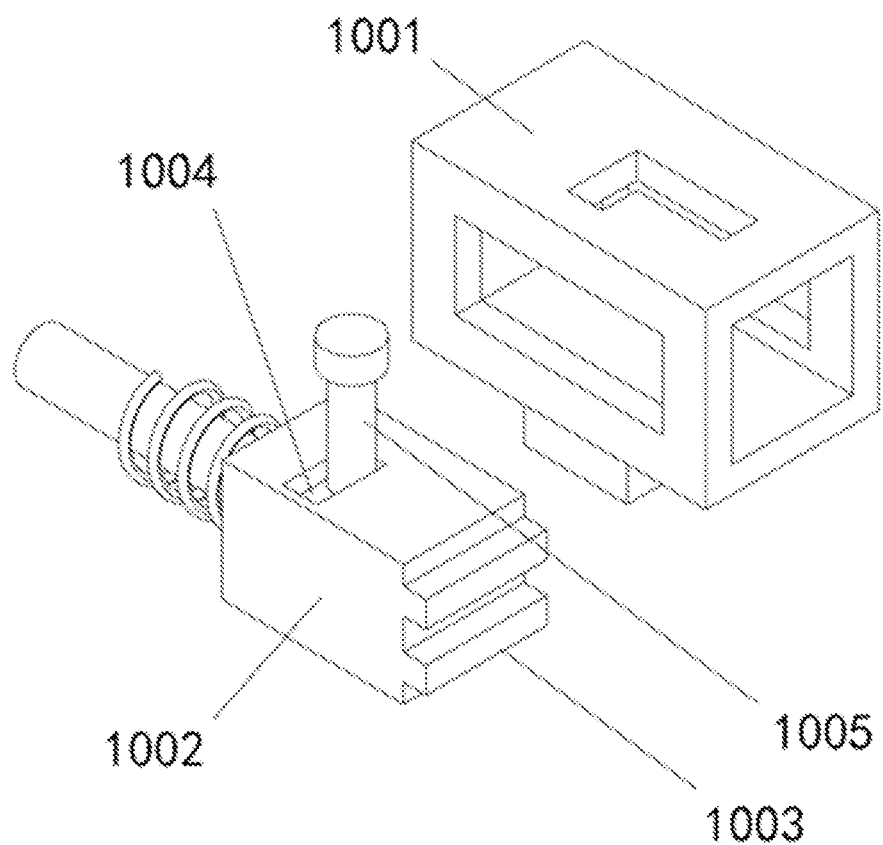
Figure 10:
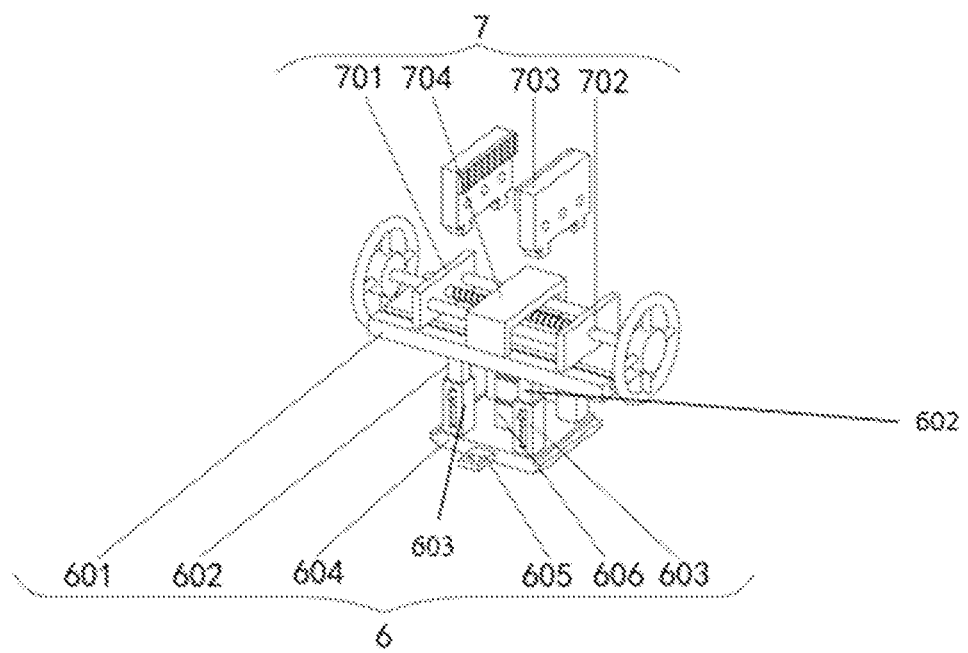

The invention provides a multifunctional rock mechanics tester consisting of a base (1), wherein a power mechanism (2) is mounted on the top of the base (1), two tension testing mechanisms (3) are arranged on the power mechanism (2) in an up-and-down symmetrical way, a clamping mechanism (4) is mounted on each tension testing mechanism (3), a rock testing block (8) is clamped between the two clamping mechanisms (4), a controller (5) is mounted on the right side of the power mechanism (2), a rectangular cavity is set at the lower part of the front end of the base (1) and internally connected with a storage box (101) in a sliding way, two pressure testing mechanisms (6) are placed on the bottom of the storage box (101), a clamping mechanism (7) is set on each pressure testing mechanism (6), two limit components (9) are mounted on the power mechanism (2) in an up-and-down symmetrical way, and a locking component (10) is set on each clamping mechanism (4);

The tension testing mechanism (3) comprises a connecting seat A (301), four first sliding sleeves (302), four first sliding pillars (303), a pull plate (304), a tension sensor (305) and a connector plate A (306), wherein the connecting seat A (301) is connected between two adjacent connecting slides (205) in a sliding way and fixedly connected with the four first sliding sleeves (302) at the top, each first sliding sleeve (302) is internally connected a first sliding pillar (303) in a sliding way, the pull plate (304) is fixedly connected with the top of the four first sliding sleeves (302) and provided with two second T chutes, the tension sensor (305) is connected between the connecting seat A (301) and the pull plate (304), the connector plate A (306) is arranged in the middle of the rear of the connecting seat A (301), and a rectangular socket is set on the top of the connector plate A (306), which is used to perform tension test on the rock sample (8);

The pressure testing mechanism (6) comprises a rectangular support plate (601), four second sliding pillars (602), four second sliding sleeves (603), a connecting seat B (604), a connector plate B (605) and a pressure sensor (606), wherein the four second sliding pillars (602) are fixedly connected with the bottom of the rectangular support plate (601), a second sliding sleeve (603) is internally connected with each second sliding pillar (602) in a sliding way, the connecting seat B (604) is fixedly connected with the bottom of the four second sliding sleeves (603), strip sliders are set on both sides of the connecting seat B (604), the connector plate B (605) is arranged in the front end of the connecting seat B (604), a rectangular socket is set on the top of the connector plate B (605), the pressure sensor (606) is arranged between the rectangular support plate (601) and the connecting seat B (604), and two third T chutes are arranged on the rectangular support plate (601), which is used to perform pressure test on the rock sample (8);

In addition, according to embodiments of the invention, as shown in FIGS. 1 and 3, the power mechanism (2) comprises a support frame (201), a first hydraulic cylinder (202), a second hydraulic cylinder (203), two driving plates (204), a connecting slide (205) and a baffle (206), wherein the support frame (201) is fixedly connected to the top of the base (1), the first hydraulic cylinder (202) and the second hydraulic cylinder (203) are respectively mounted on the upper and lower sides of the support frame (201), and the control valves on the first hydraulic cylinder (202) and the second hydraulic cylinder (203) are electrically connected with the controller (5); the opposite end of the telescopic rods on the first hydraulic cylinder (202) and the second hydraulic cylinder (203) are fixedly connected with a corresponding driving plate (204), two connecting slides (205) are mounted on the opposite sides of the two driving plates (204), a baffle (206) is fixedly connected with each rear ends of two adjacent connecting slides (205), and two T sliders are arranged on each sides of each driving plate (204); two first T chutes are arranged on both sides inside the support frame (201), four vertical guide rods are symmetrically arranged on both sides inside the support frame (201) and connected with the two driving plates (204) in a sliding way, and four T sliders on each driving plate (204) are connected with four first T chutes inside the support frame (201) in a sliding way; the power mechanism (2) is provided to drive the tension testing mechanism (3) to complete the tension test, and drive the pressure testing mechanism (6) to complete the pressure test; a controller is mounted on the right end of the support frame (201) and electrically connected with the pressure sensor (606) and the tension sensor (305);

As shown in FIGS. 6 and 7, the clamping mechanism (4) comprises two vertical support plates A (401), a clamping screw (402), two L-shaped clamping blocks (403) and a limit gear (404), wherein the two vertical support plates A (401) are fixedly connected to the pull plate (304), the clamping screw (402) is rotatably connected between the two vertical support plates A (401), externally provided with two reverse threads in a left-to-right symmetrical manner, and externally connected with two L-shaped clamping blocks (403) through the two reverse threads, two T sliders are set at the bottom of each L-shaped clamping block (403) and connected with two second T chutes on the top of the pull plate (304) in a sliding way, and the limit gear (404) is mounted on the external right of the clamping screw (402), which is used to clamp the rock sample (8);

As shown in FIGS. 1 and 10, the clamping mechanism (7) comprises two vertical support plates B (701), a clamping screw (702), two clamping blocks (703) and a box-shaped pad (704), wherein the two vertical support plates B (701) are fixedly connected to the rectangular support plate (601), the clamping screw (702) is rotatably connected between the two vertical support plates B (701), externally provided with two reverse threads in a left-to-right symmetrical manner, and externally connected with two clamping blocks (703) through the two reverse threads, two T sliders are set at the bottom of each clamping block (703) and connected with two third T chutes on the rectangular support (601) in a sliding way, and the box-shaped pad (704) is fixedly connected at the middle of the top of the rectangular support plate (601), which is used to clamp the rock sample (8);

As shown in FIGS. 4 and 5, the limit component (9) comprises a limit housing (901), a limit slider (902) and an L-shaped pull bar (903), wherein the limit housing (901) is fixedly connected in the middle of the rear end of the driving plate (204) and internally connected with the limit slider (902) in a sliding way, the front side angle at the top of the limit slider (902) is rounded, and the bottom of the limit slider (902) is fixedly connected to an L-shaped pull bar (903) that runs through the bottom of the limit housing (901) and sleeved with a spring inside the limit housing (901); when the tension testing mechanism (3) is mounted on the driving plate (204), the rear end of the connector plate A (306) runs through the baffle (206), and the head end of the limit slider (902) is inserted into the rectangular socket on the connector plate A (306), so that the tension testing mechanism (3) can be effectively limited between the two connecting slides (205);

As shown in FIGS. 8 and 9, the locking component (10) comprises a locking housing (1001), a locking slider (1002), two locking strips (1003), a sliding groove (1004), and a sliding pillar (1005), wherein the locking housing (1001) is fixedly connected to the pull plate (304), internally connected to a locking slider (1002) in a sliding way and provided an L-shaped opening at the top, two locking strips (1003) are set at the rear of the locking slider (1002) and closely contacted with the outer peripheral surface of the limit gear (404) at the rear, the front end of the locking slider (1002) is equipped with a guide rod that runs through the front side wall of the locking housing (1001) and is sleeved with a spring inside the locking housing (1001), the top of the locking slider (1002) is equipped with a sliding groove (1004) which is internally connected to a sliding pillar (1005) in a sliding way, and the sliding pillar (1005) runs through the L-shaped opening on the locking housing (1001); the locking component (10) is effective in preventing the L-shaped clamping block (403) from loosening, thereby improving the reliability of this mechanics tester during tensile test.

The specific usage and function of this embodiment: In the invention, when the rock sample (8) is subjected to tensile test, clamp the rock sample (8) between the two clamping mechanisms (4), specifically between two L-shaped clamping blocks (403), rotate the clamping screw (402) to make the two clamping blocks (703) move in opposite directions under the action of two reverse threads outside the clamping screw (702) to clamp the rock sample (8); retract the telescopic rods on the first hydraulic cylinder (202) and the second hydraulic cylinder (203) to make the two driving plates (204) respectively drive the two tension testing mechanisms (3) and the two clamping mechanisms (4) to move in opposite directions, then drive the upper and lower ends of the rock sample (8) by the two clamping mechanisms (4) to perform tension test, and the tension applied to the rock sample (8) is tested in real time by the two tension sensors (606), and the tension value is displayed on the display screen of the controller (5), thus completing the tension test on the rock sample (8);

When a pressure test is required on the rock sample (8), first manually pull the L-shaped pull bar (903) towards the end to pull the limit slider (902) end out from the rectangular socket on the connector plate A (306) and make the connecting seat A (301) not fix the two connecting slides, and slide the connecting seat A (301) forward and remove it, thereby removing the two tension testing mechanisms (3); secondly, mount the two pressure testing machines (6) placed inside the storage box (101) respectively between the two connecting slides (205) on the two driving plates (204); during mounting, slide the connecting seat B (604) between the two connecting slides (205) by the strip sliders on both sides, make the connector plate (B605) pass through the baffle (206), and insert the top of the limit slider (902) into the rectangular socket on the connector plate B (605), completing the mounting of the pressure testing mechanism (6); thirdly, put the rock sample (8) on the top of the box-shaped pad (704) in the lower clamping mechanism (7), rotate the clamping screw (702) to make the two clamping blocks (703) move in opposite directions under the action of two reverse threads outside the clamping screw (702) to clamp the lower end of the rock sample (8); then extend the telescopic rods on the first hydraulic cylinder (202) and the second hydraulic cylinder (203) to make the two driving plates (204) respectively drive the two pressure testing mechanisms (6) and the two clamping mechanisms (7) to move in opposite directions, press the rock sample (8) with the opposite faces of the upper and lower box-shaped pads (704), and the pressure applied to the rock sample (8) is tested in real time by the two pressure sensors (606), and then the pressure value is displayed on the display screen of the controller (5), thus completing the pressure test on the rock sample (8);

When a uniaxial compression test is required, extend the telescopic rod on the first hydraulic cylinder (202) to make the upper driving plate (204) drive the upper pressure testing mechanism (6) and the upper clamping mechanism (7) to move downward, thus completing the uniaxial compression test on the rock sample (8);

After the rock sample (8) is gripped by the clamping mechanism (4), the rear end of the two locking strips (1003) can be closely contacted with the outer peripheral surface of the limit gear (404) by sliding the sliding pillar (1005) to the back end of the L-shaped opening on the locking housing (1001), so that the limit gear (404) can be effectively locked to effectively prevent the clamping screw (402) from loosening.

The above are only exemplary embodiments of the invention and are not intended to limit the scope of protection of the invention, and the scope of protection is determined by the appended claims.

What is claimed is:

1. A multifunctional rock mechanics tester, consisting of a base (1), a power mechanism (2) is mounted on a top of the base (1), two tension testing mechanisms (3) are arranged on the power mechanism (2) in an up-and-down symmetrical way; a rectangular cavity is set at a lower part of a front end of the base (1) and internally connected with a storage box (101) in a sliding way, two pressure testing mechanisms (6) are placed on a bottom of the storage box (101), a clamping mechanism (7) is set on each pressure testing mechanism (6), two limit components (9) are mounted on the power mechanism (2) in an up-and-down symmetrical way, and a locking component (10) is set on each clamping mechanism (4); each limit component (9) comprises a limit housing (901), a limit slider (902) and a L-shaped pull bar (903), wherein the limit housing (901) is fixedly connected in a middle of a rear end of each of two driving plates (204) and internally connected with the limit slider (902) in a sliding way, a front side angle at a top of the limit slider (902) is rounded, and a bottom of the limit slider (902) is fixedly connected to the L-shaped pull bar (903) that runs through a bottom of the limit housing (901) and sleeved with a spring inside the limit housing (901);

each tension testing mechanism (3) comprises a connecting seat A (301), four first sliding sleeves (302), four first sliding pillars (303), a pull plate (304), a tension sensor (305) and a connector plate A (306), wherein the connecting seat A (301) is connected between two adjacent connecting slides (205) in a sliding way and fixedly connected with the four first sliding sleeves (302) at a top, each first sliding sleeve (302) is internally connected to a corresponding first sliding pillar (303) in a sliding way, the pull plate (304) is fixedly connected with a top of the four first sliding sleeves (302) and provided with two second T chutes, the tension sensor (305) is connected between the connecting seat A (301) and the pull plate (304), the connector plate A (306) is arranged in a middle of a rear of the connecting seat A (301), and a rectangular socket is set on a top of the connector plate A (306);

each pressure testing mechanism (6) comprises a rectangular support plate (601), four second sliding pillars (602), four second sliding sleeves (603), a connecting seat B (604), a connector plate B (605), and a pressure sensor (606), wherein the four second sliding pillars (602) are fixedly connected with a bottom of the rectangular support plate (601), each second sliding sleeve (603) is internally connected with a corresponding second sliding pillar (602) in a sliding way, the connecting seat B (604) is fixedly connected with a bottom of the four second sliding sleeves (603), strip sliders are set on both sides of the connecting seat B (604), the connector plate B (605) is arranged in a front end of the connecting seat B (604), a rectangular socket is set on a top of the connector plate B (605), the pressure sensor (606) is arranged between the rectangular support plate (601) and the connecting seat B (604), and two third T chutes are arranged on the rectangular support plate (601).

2. The multifunctional rock mechanics tester according to claim 1, wherein a strip opening (102) is made on both sides of the base (1) and connected to the rectangular cavity; a limit sliding pillar (103) is set on both ends of the storage box (101), and two limit sliding pillars (103) are connected with two strip openings (102) in a sliding way.

3. The multifunctional rock mechanics tester according to claim 1, wherein the power mechanism (2) comprises a support frame (201), a first hydraulic cylinder (202), a second hydraulic cylinder (203), two driving plates (204), one or more connecting slides (205) and a baffle (206), wherein the support frame (201) is fixedly connected to the top of the base (1), the first hydraulic cylinder (202) and the second hydraulic cylinder (203) are respectively mounted on upper and lower sides of the support frame (201), and control valves on the first hydraulic cylinder (202) and the second hydraulic cylinder (203) are electrically connected with a controller (5); an opposite end of telescopic rods on the first hydraulic cylinder (202) and the second hydraulic cylinder (203) are fixedly connected with a corresponding driving plate (204), two connecting slides (205) are mounted on opposite sides of each driving plate (204), the baffle (206) is fixedly connected with each rear ends of two adjacent connecting slides (205), and two T sliders are arranged on each sides of each driving plate (204).

4. The multifunctional rock mechanics tester according to claim 3, wherein two first T chutes are arranged on both sides inside the support frame 201, four vertical guide rods are symmetrically arranged on both sides inside the support frame (201) and connected with the two driving plates (204) in a sliding way, and four T sliders on each driving plate (204) are connected with four first T chutes inside the support frame (201) in a sliding way.

5. The multifunctional rock mechanics tester according to claim 3, wherein when each tension testing mechanism (3) is mounted on the corresponding driving plate (204), a rear end of the connector plate A (306) runs through the baffle (206), and a head end of the limit slider (902) is inserted into the rectangular socket on the connector plate A (306).

6. The multifunctional rock mechanics tester according to claim 1, wherein each clamping mechanism (4) comprises two vertical support plates A (401), a clamping screw (402), two L-shaped clamping blocks (403) and a limit gear (404), wherein the two vertical support plates A (401) are fixedly connected to the pull plate (304), the clamping screw (402) is rotatably connected between the two vertical support plates A (401), externally provided with two reverse threads in a left-to-right symmetrical manner, and externally connected with two L-shaped clamping blocks (403) through the two reverse threads, two T sliders are set at a bottom of each L-shaped clamping block (403) and connected with the two second T chutes on a top of the pull plate (304) in a sliding way, and the limit gear (404) is mounted on the external right of the clamping screw (402).

7. The multifunctional rock mechanics tester according to claim 5, wherein each locking component (10) comprises a locking housing (1001), a locking slider (1002), two locking strips (1003), a sliding groove (1004), and a sliding pillar (1005), wherein the locking housing (1001) is fixedly connected to the pull plate (304), internally connected to the locking slider (1002) in a sliding way and provided an L-shaped opening at a top, the two locking strips (1003) are set at a rear of the locking slider (1002) and closely contacted with an outer peripheral surface of the limit gear (404) at a rear, a front end of the locking slider (1002) is equipped with a guide rod that runs through a front side wall of the locking housing (1001) and is sleeved with a spring inside the locking housing (1001), a top of the locking slider (1002) is equipped with the sliding groove (1004) which is internally connected to the sliding pillar (1005) in a sliding way, and the sliding pillar (1005) runs through the L-shaped opening on the locking housing (1001).

8. The multifunctional rock mechanics tester according to claim 1, wherein each clamping mechanism (7) comprises two vertical support plates B (701), a clamping screw (702), two clamping blocks (703) and a box-shaped pad (704), wherein the two vertical support plates B (701) are fixedly connected to the rectangular support plate (601), the clamping screw (702) is rotatably connected between the two vertical support plates B (701), externally provided with two reverse threads in a left-to-right symmetrical manner, and externally connected with the two clamping blocks (703) through the two reverse threads, two T sliders are set at a bottom of each clamping block (703) and connected with two third T chutes on the rectangular support (601) in a sliding way, and the box-shaped pad (704) is fixedly connected at a middle of a top of the rectangular support plate (601).

\* \* \* \* \*